United States Patent [19]

Kamitamari et al.

[11] Patent Number: 5,254,700
[45] Date of Patent: Oct. 19, 1993

[54] PROCESS FOR PRODUCTION OF N-SUBSTITUTED CARBAZOLES

[75] Inventors: Masashi Kamitamari, Ibaraki; Takashi Kamikawa, Toyonaka; Osamu Maruyama, Takatsuki; Shinzaburo Masaki, Toyonaka; Junji Shiraiwa, Kawachinagano, all of Japan

[73] Assignee: Sumitomo Chemical Company, Limited, Osaka, Japan

[21] Appl. No.: 20,117

[22] Filed: Feb. 19, 1993

[30] Foreign Application Priority Data

Feb. 27, 1992 [JP] Japan ............................ 4-041155

[51] Int. Cl.$^5$ ................. C07D 209/86; C07D 209/88
[52] U.S. Cl. ..................................... 548/440; 548/445
[58] Field of Search ............................. 548/440, 445

[56] References Cited

PUBLICATIONS

CA. 63, 18008C (1965).
CA. 82, 45003m (1975).
CA. 84, 30793n (1976).
Advances in Heterocyclic Chemistry, vol. 35, pp. 96–100 (1984).
Y. Hosoda "Senryo Kagaki", Gihodo (1966), p. 799 (with partial English translation).
Bull. Chem. Soc. Jpn. 54, pp. 1897–1898 (1981).
CA. 18, 81 (1924).
CA. 32, 7915 (1938).
CA. 63, 565d (1965).

Primary Examiner—Robert W. Ramsuer
Attorney, Agent, or Firm—Birch, Stewart, Kolasch & Birch

[57] ABSTRACT

There is disclosed a process for the production of N-substituted carbazoles with high efficiency, in which a carbazole compound is reacted with an appropriate halogenated compound in an inert solvent in the presence of an acid-removing agent and an amine without using any quaternary ammonium salt which is required in the conventional process.

20 Claims, No Drawings

PROCESS FOR PRODUCTION OF N-SUBSTITUTED CARBAZOLES

FIELD OF THE INVENTION

The present invention relates to a process for the production of N-substituted carbazoles with high efficiency.

BACKGROUND OF THE INVENTION

As a conventional process of producing N-substituted carbazoles, there has been a process in which a carbazole compound is reacted with an alkyl halide in the presence of a quaternary ammonium salt such as benzyltriethylammonium chloride using 50% aqueous sodium hydroxide as an acid-removing agent (*Bull. Chem. Soc. Jpn.*, 54, 1879 (1981)). This process, however, requires the use of a certain quaternary ammonium salt which is relatively expensive, and it can attain only a low yield, even if the alkyl halide used is relatively reactive, such as ethyl bromide, methyl iodide or allyl chloride; therefore, it cannot always be said that this process is suitable for the production on an industrial scale.

SUMMARY OF THE INVENTION

Under these circumstances, the present inventors have intensively studied to solve the problems of the conventional process as described above and to provide a process for the production of N-substituted carbazoles at a low cost with high yield. As the result, they have found that N-substituted carbazoles can be obtained with high yield by reacting a carbazole compound with an appropriate halogenated compound in the presence of an amine without using any quaternary ammonium salt, thereby completing the present invention.

That is, the present invention provides a process for the production of N-substituted carbazoles of the general formula:

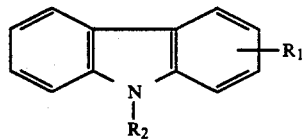

(IV)

wherein $R_1$ is a hydrogen atom, a $C_1$-$C_6$ alkyl group, a nitro group, a $C_1$-$C_6$ alkoxy group or a halogen atom, and $R_2$ is a $C_1$-$C_6$ alkyl group, a $C_2$-$C_6$ alkenyl group or a $C_7$-$C_8$ aralkyl group, comprising the step of reacting a carbazole compound of the general formula:

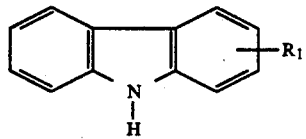

(I)

wherein $R_1$ is the same as defined above, with a halogenated compound of the general formula:

$$R_2-X \quad (II)$$

wherein $R_2$ is the same as defined above and X is a halogen atom, in an inert solvent in the presence of an acid-removing agent and an amine of the general formula:

$$R_3R_4R_5N \quad (III)$$

wherein $R_3$, $R_4$ and $R_5$ are the same or different and are a hydrogen atom, a $C_1$-$C_6$ alkyl group or a $C_7$-$C_8$ aralkyl group.

DETAILED DESCRIPTION OF THE INVENTION

According to the process of the present invention, N-substituted carbazoles (IV) can be obtained by reacting the carbazole compound (I) with the halogenated compound (II) in an inert solvent in the presence of a certain acid-removing agent and the amine (III).

The substituent $R_1$ of the carbazole compound (I) as the raw material used in the reaction is a hydrogen atom; a $C_1$-$C_6$ alkyl group such as a methyl group or an ethyl group; a $C_1$-$C_6$ alkoxy group such as a methoxy group or an ethoxy a group; a nitro group or a halogen atom. Typical examples of the carbazole compound (I) are carbazole, 3-nitrocarbazole, 1-nitrocarbazole, 2-methoxycarbazole, 1-methylcarbazole, 3-methylcarbazole, 1-chlorocarbazole and 3-chlorocarbazole.

The substituent $R_2$ of the halogenated compound (II) is a $C_1$-$C_6$ alkyl group such as a methyl group, an ethyl group, a propyl group, an isopropyl group or a butyl group; a $C_2$-$C_6$ alkenyl group such as an allyl group or a 2-butenyl group; or a $C_7$-$C_8$ aralkyl group such as a benzyl group, a 1-phenethyl group or a 2-phenethyl group.

The substituent X of the halogenated compound (II) is a halogen atom such as a chlorine atom, a bromine atom or an iodine atom, with preferred being a chlorine atom.

The amount of halogenated compound to be used is usually in the range of from 1 to 10 moles, preferably from 1 to 5 moles, and more preferably from 1 to 2 moles, per mole of the carbazole compound as the raw material.

The substituents $R_3$, $R_4$ and $R_5$ of the amine (III) are the same or different and are a hydrogen atom; a $C_1$-$C_6$ alkyl group such as a methyl group, an ethyl group, a n-propyl group, an i-propyl group, a n-butyl group, an i-butyl group, a sec-butyl group, a t-butyl group, a n-pentyl group, an i-amyl group, a sec-amyl group, a t-amyl, neo-pentyl group, a n-hexyl group, a 1-methylpentyl group, a 2-methylpentyl group or a 3-methylpentyl group; or a $C_7$-$C_8$ aralkyl group such as a benzyl group, a 1-phenethyl group or a 2-phenethyl group.

Typical examples of the amine (III) are mono($C_1$-$C_6$)alkylamines such as methylamine, ethylamine, n-propylamine, i-propylamine and n-butylamine; di($C_1$-$C_6$)alkylamines such as dimethylamine, diethylamine, di-n-propylamine, di-i-propylamine and di-n-butylamine; and tri($C_1$-$C_6$)alkylamines such as trimethylamine, N-methyldiethylamine, N,N-dimethylethylamine, triethylamine, tri-n-propylamine, tri-n-butylamine, N-ethyldiisopropylamine and N,N-diethylbutylamine. Besides these amines, any other amine can also be used, such as N,N-dimethylbenzylamine, N,N-diethylbenzylamine, 1-phenethylamine or 2-phenethylamine. Among these amines, preferred are n-butylamine, diethylamine, di-n-butylamine, triethylamine, tri-n-butylamine N,N-diethylbenzylamine and N,N-dimethylbenzylamine.

The amount of amine to be used is usually in the range of from 0.1% to 30% by mole, preferably from 1% to 20% by mole, based on the mole of the carbazole compound as the raw material.

As the acid-removing agent, inorganic bases can usually be used. Typical examples of the acid-removing agent are hydroxides of alkali metals, such as sodium hydroxide, potassium hydroxide and lithium hydroxide; hydroxides of alkaline earth metals, such as barium hydroxide and calcium hydroxide; carbonates of alkali metals, such as sodium carbonate and potassium carbonate; and hydrogencarbonates of alkali metals, such as sodium hydrogencarbonate and potassium hydrogencarbonate. Among these inorganic bases, preferred are hydroxides of alkali metals with particularly preferred being sodium hydroxide and potassium hydroxide. These acid-removing agents may be used solely or in admixture with each other. Although these acid-removing agents can be used as they are in solid state, they are preferably used in the form of an aqueous solution.

The amount of acid-removing agent to be used is usually in the range of from 1 to 5 moles, preferably from 1 to 3 moles, per mole of the carbazole compound as the raw material.

The solvent to be used in the above reaction is not particularly limited, so long as it is an inert solvent. Preferred examples of the solvent are aromatic hydrocarbons such as benzene, toluene and xylene; halogenated aromatic hydrocarbons such as monochlorobenzene, dichlorobenzene and trichlorobenzene; and aromatic nitro compounds such as nitrobenzene. Particularly preferred are halogenated aromatic hydrocarbons.

The solvent is usually used at a 0.5- to 20-fold weight, preferably 1- to 5-fold weight, based on the weight of the carbazole compound as the raw material.

The above reaction is usually carried out at a temperature of from room temperature to 200° C., preferably from 30° to 150° C., under normal pressure or under pressure up to about 20 kg/cm$^2$.

After completion of the reaction, for example, the cooled reaction mass is transferred into a separatory funnel. The reactor is washed with the reaction solvent and water. The washings are combined with the reaction mass, and the separated organic layer is washed with a mineral acid solution to neutralize base traces. The obtained N-substituted carbazole solution may be transferred to the subsequent step or concentrated to give the product.

Thus, N-substituted carbazoles (IV) can be obtained, such as N-methylcarbazole, N-ethylcarbazole, N-propylcarbazole, N-butylcarbazole, N-allylcarbazole and N-benzylcarbazole.

According to the present invention, N-substituted carbazoles (IV) can be produced at a low cost with high yield.

The present invention will be further illustrated by way of the following examples which are not to be construed to limit the scope thereof.

EXAMPLE 1

A 0.5-liter autoclave equipped with a stirrer was charged with carbazole (82.0 g), o-dichlorobenzene (100 g), ethyl chloride (40.2 g), 48% sodium hydroxide (73.9 g) and triethylamine (5 g). After the atmosphere in the autoclave was replaced with nitrogen gas, the autoclave was heated to the reaction temperature of 100° C. and the reaction mixture was stirred at the same temperature for 9 hours, while keeping the temperature. After completion of the reaction, the mixture was cooled to 50° C., and was transferred into a separatory funnel. The autoclave was washed with o-dichlorobenzene and water. The washings were combined with the reaction mass, and the combined mixture was separated. The separated organic layer was washed with a 25% sulfuric acid solution to neutralize base traces, and the water layer was removed by separation to give 273.0 g of an o-dichlorobenzene solution of N-ethylcarbazole. The analysis of this solution by chromatography revealed that the content of N-ethylcarbazole was 34.9% and the yield thereof was 99.6%.

EXAMPLE 2

A 0.5-liter autoclave equipped with a stirrer was charged with carbazole (82.4 g), o-dichlorobenzene (100 g), ethyl chloride (40.2 g), 48% sodium hydroxide (55.8 g) and tributylamine (9.2 g). After the atmosphere in the autoclave was replaced with nitrogen gas, the autoclave was heated to the reaction temperature of 100° C. and the reaction mixture was stirred at the same temperature for 9 hours, while keeping the temperature. After completion of the reaction, the mixture was cooled to 50° C. The same procedures as those described in Example 1 gave 275.9 g of an o-dichlorobenzene solution of N-ethylcarbazole. The analysis of this solution by chromatography revealed that the content of N-ethylcarbazole was 32.9% and the yield thereof was 94.3%.

EXAMPLE 3

N-ethylcarbazole was obtained by the same reaction under the same conditions as described in Example 2, except that n-butylamine was used in place of tributylamine, and ethyl chloride and sodium hydroxide were used at an amount of 1.5 moles and 2.0 moles, respectively, per mole of carbazole. The conversion of carbazole was 93.1% and the yield of N-ethylcarbazole was 90.9%.

EXAMPLE 4

N-ethylcarbazole was obtained by the same reaction under the same conditions as described in Example 2, except that diethylamine was used in place of tributylamine, and ethyl chloride and sodium hydroxide were used at an amount of 1.4 moles and 1.9 moles, respectively, per mole of carbazole. The conversion of carbazole was 98.1% and the yield of N-ethylcarbazole was 99.0%.

EXAMPLE 5

N-ethylcarbazole was obtained by the same reaction under the same conditions as described in Example 2, except that N,N-dimethylbenzylamine was used in place of tributylamine, and ethyl chloride and sodium hydroxide were used at an amount of 1.3 moles and 1.8 moles, respectively, per mole of carbazole. The conversion of carbazole was 100.0% and the yield of N-ethylcarbazole was 96.2%.

EXAMPLES 6-8

Various N-substituted carbazoles such as N-ethyl-2-methylcarbazole (Example 6), N-ethyl-1-methoxycarbazole (Example 7) and N-ethyl-3-chlorocarbazole (Example 8) were obtained by the same reaction under the same conditions as described in Example 1, except that 2-methylcarbazole, 1-methoxycarbazole and 3- chlorocarbazole were used, respectively, in place of carbazole.

What is claimed is:

1. A process for the production of an N-substituted carbazole compound of the formula:

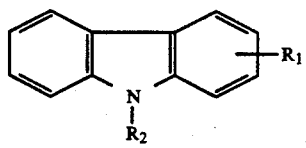

(IV)

wherein $R_1$ is a hydrogen atom, a $C_1-C_6$ alkyl group, a nitro group, a $C_1-C_6$ alkoxy group or a halogen atom, and $R_2$ is a $C_1-C_6$ alkyl group, a $C_2-C_6$ alkenyl group or a $C_7-C_8$ aralkyl group, comprising the step of reacting a carbazole compound of the formula:

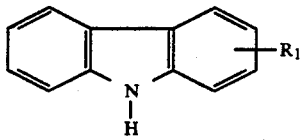

(I)

wherein $R_1$ is the same as defined above, with a halogenated compound of the formula:

  (II)

wherein $R_2$ is the same as defined above and X is a halogen atom, in an inert solvent in the presence of an acid-removing agent and an amine of the formula:

  (III)

wherein $R_3$, $R_4$ and $R_5$ are the same or different and are a hydrogen atom, a $C_1-C_6$ alkyl group or a $C_7-C_8$ aralkyl group with the proviso that $R_3$, $R_4$ and $R_5$ cannot all simultaneously be a hydrogen atom.

2. A process according to claim 1, wherein at least one of the $R_3$, $R_4$ and $R_5$ is a $C_1-C_6$ alkyl group.

3. A process according to claim 2, wherein all of the $R_3$, $R_4$ and $R_5$ are ethyl groups.

4. A process according to claim 1, wherein at least one of the $R_3$, $R_4$ and $R_5$ is a benzyl group.

5. A process according to claim 4, wherein one of the $R_3$, $R_4$ and $R_5$ is a benzyl group and the other two are methyl groups.

6. A process according to claim 4, wherein one of the $R_3$, $R_4$ and $R_5$ is a benzyl group and the other two are ethyl groups.

7. A process according to claim 1, wherein the inert solvent is an aromatic hydrocarbon optionally substituted with at least one halogen atom.

8. A process according to claim 1, wherein the acid-removing agent is a hydroxide of alkali metals.

9. A process according to claim 2, wherein all of the $R_3$, $R_4$ and $R_5$ are butyl groups.

10. A process according to claim 2, wherein the $R_3$ is a hydrogen atom and the other two are butyl groups.

11. A process according to claim 2, wherein the $R_3$ is a hydrogen atom and the other two are ethyl groups.

12. A process according to claim 2, wherein the $R_3$ is a butyl group and the other two are hydrogen atoms.

13. The process according to claim 1, wherein $R_3$, $R_4$ and $R_5$ are selected from the group consisting of a hydrogen atom, a methyl group, an ethyl group, a n-propyl group, an i-propyl group, a n-butyl group, an i-butyl group, a sec-butyl group, a t-butyl group, a n-pentyl group, an i-amyl group, a sec-amyl group, a t-amyl, a neo-pentyl, a n-hexyl group, a 1-methylpentyl group, a 2-methylpentyl group, a 3-methylpentyl group, a benzyl group, a 1-phenethyl group and a 2-phenethyl group.

14. The process according to claim 1, wherein the halogenated compound (II) is present in an amount of 1 to 10 moles per mole of the carbazole compound (IV).

15. The process according to claim 1, wherein the halogenated compound (II) is present in an amount of 1 to 2 moles per mole of the carbazole compound (IV).

16. The process according to claim 1, wherein the amine (III) is selected from the group consisting of methylamine, ethylamine, n-propylamine, i-propylamine, n-butylamine, dimethylamine, diethylamine, di-n-propylamine, di-i-propylamine, di-n-butylamine, trimethylamine, N-methyl-diethylamine, N,N-dimethylethylamine, triethylamine, tri-n-propylamine, tri-n-butylamine, N-ethyldiisopropylamine, N,N-diethylbutylamine, N,N-dimethylbenzylamine, N,N-diethylbenzylamine, 1-phenethylamine and 2-phenethylamine.

17. The process according to claim 1, wherein the amine (III) is present in an amount of from 0.1% to 30% by mole based on a mole of the carbazole compound (IV).

18. The process according to claim 1, wherein the amine (III) is present in an amount of from 1% to 20% by mole based on a mole of the carbazole compound (IV).

19. The process according to claim 1, wherein the inert solvent is present in an amount of from 0.5- to 20-fold weight based on the weight of the carbazole compound (IV).

20. The process according to claim 1, wherein the process is carried out at a temperature of from room temperature to 200° C. under a pressure of up to 20 kg/cm².

* * * * *